US006492117B1

(12) United States Patent
Choo et al.

(10) Patent No.: US 6,492,117 B1
(45) Date of Patent: Dec. 10, 2002

(54) ZINC FINGER POLYPEPTIDES CAPABLE OF BINDING DNA QUADRUPLEXES

(75) Inventors: Yen Choo, London (GB); Mark Isalan, London (GB); Sachin D. Patel, Mumbai (IN); Shhankar Balasubramanian, Cambridge (GB); Xiaohai Liu, Cambridge (GB)

(73) Assignee: Gendaq Limited, London (GB)

( * ) Notice: Subject to any disclaimer, the term of this patent is extended or adjusted under 35 U.S.C. 154(b) by 0 days.

(21) Appl. No.: 09/614,679

(22) Filed: Jul. 12, 2000

(51) Int. Cl.[7] .................. C12Q 1/68; G01N 33/566; C07K 7/00; C07K 16/00; C07K 17/00; C07K 5/00; A61K 38/00
(52) U.S. Cl. ..................... 435/6; 436/501; 530/300; 530/324
(58) Field of Search ............... 435/6; 436/501, 436/101; 530/300, 324; 130/300, 324

(56) References Cited

U.S. PATENT DOCUMENTS 6,001,657 A * 12/1999 Hardin et al. ............... 436/501
6,288,042 B1 * 9/2001 Rando et al. ................. 514/44

FOREIGN PATENT DOCUMENTS

| WO | WO9606166 | 2/1996 |
| WO | WO9833503 | 8/1998 |
| WO | WO9853057 | 11/1998 |

OTHER PUBLICATIONS

Salazar, M. et al., "Thermally Induced DNA.RNA Hybrid to G–Quadruplex Transitions: Possible Implications for Telomere Synthesis by Telomerase", Biochemistry vol. 35, pp. 16110–16115 (1996).*
Giraldo, R. et al., "The yeast telomere–binding protein RAP1 binds to and promotes the formation of DNA quadruplexes in telomeric DNA", The EMBO J., vol. 13, pp. 2411–2420 (1994).*
Sussel, L. et al., "Separation of transcriptional activation and silencing functions of the RAP1–encoded repressor/activator protein 1: Isolation of viable mutants affecting both silencing and telomere length", PNAS USA, vol. 88, pp. 7749–7753 (1991).*
König et al., "The crystal structure of the DNA–binding domain of yeast RAP1 in complex with telomeric DNA", Cell, vol. 85, 1996, p. 125–136.
Isalahn et al., "Selection of zinc fingers that bind single–stranded telomeric DNA in the G–quadruplex conformation," Biochemistry, vol. 40, No. 3, Jan. 23, 2001, pp. 830–836.
Mazumder et al., "Inhibition of the human immunodeficiency virus type 1 integrase by guanosine quartet structures," Biochemistry, Am Chem Soc, vol. 35, No. 43, Oct. 29, 1996, pp. 13762–13771.
Zahler et al., "Inhibition of telomerase by g–quartet DNA structures," Nature, London, vol. 350, Apr. 25, 1991, pp. 718–720.
Brown et al., "Construction and characterization of a quadruplex DNA selective single–chain autoantibody from a viable motheaten mouse hybridoma with homology to telomeric DNa binding proteins," Biochemistry, vol. 37, No. 46, Mar. 1998, pp. 16338–16348.
Brown II et al., "Isolation and characterization of a monoclonal anti–quadruplex DNA antibody from autoimmune "viable motheaten" mice," Biochemistry, vol. 37, No. 46, Mar. 1998, pp. 16325–16337.

* cited by examiner

*Primary Examiner*—Kenneth R. Horlick
*Assistant Examiner*—Teresa Strzelecka
(74) *Attorney, Agent, or Firm*—Robins & Pasternak LLP; Sean M. Brennan

(57) ABSTRACT

The present invention relates to isolated or purified molecule(s) capable of binding to one or more of telomeric, G-quadruplex, or G-quartet nucleic acid(s).

22 Claims, 6 Drawing Sheets

```
         F1                    F2                    F3
 -1  1  2  3  4  5  6   -1  1  2  3  4  5  6   -1  1  2  3  4  5  6

A  S  A  A  L  I  A    A  S  A  A  L  S  A    A  K  A  A  R  I  A
  D     D        T  E    D  R  D  D        E    D  N  D  D     K  E
  H     H        K       H     H  H        K    H  R  H  H     T  K
  N     K  N                N  K  N        N    N  S  K  N        N
  Q     N  S        Q    Q     N  S        Q    Q     N  S        Q
  R     Q  T        R    R     Q  T        R    R     Q  T        R
  T     R  V        T    T     R  V        T    T     R  V        T
        S  V                   S  V                   S  V
```

|  | F1 | | | | | | | F2 | | | | | | | F3 | | | | | | |
|---|---|---|---|---|---|---|---|---|---|---|---|---|---|---|---|---|---|---|---|---|---|
| PROTEIN | -1 | 1 | 2 | 3 | 4 | 5 | 6 | -1 | 1 | 2 | 3 | 4 | 5 | 6 | -1 | 1 | 2 | 3 | 4 | 5 | 6 |
| Gq1 | D | S | A | H | L | T | R | D | R | S | D | L | S | E | R | S | D | H | R | I | E |
| Gq2 | R | S | D | H | L | I | N | D | R | A | D | L | S | E | T | S | S | H | R | T | N |
| Gq3 | D | S | A | H | L | T | R | D | R | D | H | L | S | E | T | S | S | H | R | T | N |
| Gq4 | T | S | H | H | L | I | Q | D | R | A | D | L | S | E | H | Q | H | Y | R | T | N |
| Zif268 | R | S | D | E | L | T | R | R | S | D | H | L | T | T | R | S | D | E | R | K | R |

Table 1

| DNA sequence (5'-3') | $K_d^E$ (nM) |
|---|---|
| (GGTTAG)$_5$ | 26 |
| (GGTT<u>A</u>A)$_5$ | - |
| (<u>A</u>GTTAG)$_5$ | - |
| (<u>I</u>GTTAG)$_5$ | - |
| (GGTTAG)$_5$ duplex | - |

FIG. 7

ZINC FINGER POLYPEPTIDES CAPABLE OF BINDING DNA QUADRUPLEXES

FIELD OF THE INVENTION

The invention relates to DNA binding molecules. In particular the invention relates to molecules which bind to G-quadruplex or telomeric DNA.

BACKGROUND TO THE INVENTION

There is considerable interest in molecules that bind to telomeric DNA sequences and G-quadruplexes. Such molecules will be useful to test hypotheses of telomeric length regulation. and may have therapeutic potential.

Several naturally occurring proteins with affinity for G-quadruplexes have been described in the prior art (reviewed in Wellinger, R. J., & Sen, D. (1997) *European Journal of Cancer* 33, 735–749), although none have so far proved to be good candidates for use as diagnostic probes or therapeutic tools.

Prior art quadruplex DNA binding molecules, such as a recently reported DNA-binding autoantibody (Brown, B. A., Li, Y. Q., Brown, J. C., Hardin, C. C., Roberts, J. F., Pelsue, S. C., & Shultz, L. D. (1998) *Biochemistry* 37. 16325–16337). have only moderate binding affinities and discriminate weakly between duplex and quadruplex DNA.

DNA binding molecules are disclosed in M. D. Isalan, A. Klug and Y. Choo. International Patent Application Publication No. WO98/53057.

Naturally occurring telomere-binding proteins are also unable to discriminate these structures. For example, *Saccharomyces cerevisiae* RAP1 (Giraldo, R. & Rhodes. D. (1994) *EMBO J* 13, 2411–2420) has distinct but inseparable domains for binding quadruplexes and double stranded DNA.

The present invention seeks to overcome problems associated with the prior art.

SUMMARY OF THE INVENTION

Disclosed herein is the engineering of DNA-binding polypeptide molecule(s) that bind to telomeric G-quadruplex structure(s). Preferably, these molecules are polypeptides comprising a zinc finger motif.

Zinc finger polypeptides according to the present invention advantageously bind to single stranded human telomeric DNA with an affinity comparable to the binding of naturally occurring transcription factors to their cognate duplex DNA recognition site(s). DNA in the bound complexes is preferably in the G-quadruplex conformation.

Thus, in a first aspect, the invention relates to an isolated or purified molecule capable of binding to one or more of telomeric, G-quadruplex, or G-quartet nucleic acid.

As used herein, the term 'isolated or purified' is used to mean that a molecule is free of one or more components of its natural environment. Where the molecule(s) are produced in vitro or in vivo in a laboratory, they are considered to be isolated or purified. Isolated molecules according to the invention therefore include such molecules when produced using recombinant cell culture, phage culture etc. Molecules present in an organism expressing a recombinant nucleic acid encoding same, whether the molecule(s) are "isolated" or otherwise, are also included within the scope of the present invention.

The term 'molecule' has its natural meaning. Preferably, molecules according to the invention are polypeptides.

The expression 'capable of binding to one or more of' is used to indicate that the molecule(s) retain the ability to associate with, interact with, or bind to one or more of the mentioned entities. This binding may be reversible or irreversible. This binding may be temporary or permanent. It may be covalent, ionic, or hydrogen bonding. vander-waals association or any other type of molecular interaction.

Telomeric nucleic acid refers to nucleic acid comprised in or derived from telomeres of eukaryotic cells. The term therefore includes known telomeric repetitive DNA sequences (see below for examples), may include related RNA sequences such as telomeric primer sequences, and may include sub-telomeric repeat sequences, or other sequence(s) found at chromosome ends. The term is intended to include these nucleic acids regardless of their molecular context. This means that such molecules are included if they are in a complex with telomeric or scaffold proteins, or if they are naked in vitro. The molecules are included when they are in vivo such as bona fide telomeres in cell nuclei, or when they are removed from their natural context, such as when on a CHEF (clamped homogenous electric fields) gel or when cloned. The term telomeric nucleic acid may also include mutants, fragments or derivatives thereof, provided such mutants, fragments or derivatives retain substantial sequence homology with said telomeric nucleic acid molecules. This is discussed in more detail below.

Telomeric nucleic acids are known to adopt unconventional or non-conventional structural conformations, mediated by unusual base-pairing (ie. other than simple base paired duplex DNA). Examples of these structures include G-quadruplexes.

The term 'G-quadruplex' as understood herein relates to any four-stranded DNA structure. Those skilled in the art realise that these structures comprise loops and hairpins and such like as the two strands of a duplex fold back alongside themselves to form a four-stranded structure, even though only two distinct nucleotide polymer strands may be present. It is also understood that such structures may comprise single-stranded DNA and/or double stranded DNA. Accordingly, in another aspect, the invention relates to a nucleic acid binding molecule as described above wherein said nucleic acid comprises single-stranded DNA. The feature which characterises a 'G-quadruplex' as the term is used herein is that at least a part of the structure to which it refers is in a four-stranded conformation. G-quadruplexes may be intra- or inter-molecular.

The term 'G-quartet' refers to that part of a nucleic acid structure which is in a four-stranded conformation. A G-quartet is therefore any segment of nucleic acid or combination of nucleic acids which is in a four-stranded conformation.

Thus, in another aspect, the invention relates to a nucleic acid binding molecule as described above wherein said nucleic acid is not in a double-helical conformation.

Four-stranded nucleic acid conformations (ie. G-quartets) may comprise unconventional base pairing. Conventional base pairing is considered to be Watson and Crick double helical base paired nucleic acid. Unconventional base pairing is therefore base pairing other than Watson and Crick double helical base pairing. Thus, in another aspect, the invention relates to a nucleic acid binding molecule as described above wherein said nucleic acid is in a non-Watson-Crick base paired conformation.

An example of unconventional base pairing is Hoogsteen base pairing. Thus, in another aspect, the invention relates to a nucleic acid binding molecule as described above wherein said nucleic acid comprises Hoogsteen base pairing.

In another aspect. the invention relates to a nucleic acid binding molecule as described above wherein said nucleic acid is comprised in a chromosome end.

In another aspect. the invention relates to a nucleic acid binding molecule as described above wherein said nucleic acid is comprised in a telomeric structure.

Preferably, molecules according to the invention arc polypeptides. Thus, in another aspect, the invention relates to a nucleic acid binding molecule as described above wherein said molecule is a polypeptide.

More preferably, molecules according to the invention are polypeptides comprising a zinc finger motif. A zinc finger is a DNA-binding protein domain that may be used as a scaffold to design DNA-binding proteins. Preferably, the molecule of the invention is a polypeptide comprising a zinc finger nucleic acid binding motifs. The properties of such motifs include the possession of a Cys2-His2 motif, and are discussed in more detail below. Therefore, in another aspect, the invention relates to a nucleic acid binding molecule as described above wherein said molecule is a polypeptide comprising at least one zinc finger Motif.

Molecules of the present invention preferably exhibit strong discrimination between G-quadruplex nucleic acid and the double-stranded form of the same sequence and between G-quadruplex nucleic acid and the single-stranded variants, Accordingly, in another aspect, the invention relates to a nucleic acid binding molecule as described above wherein said molecule has an affinity for G-quadruplex nucleic acid which is different from its affinity for duplex nucleic acid. Preferably said molecule has an affinity for G-quadruplex nucleic acid which is higher than its affinity for duplex nucleic acid, In another aspect, the invention relates to a method for assaying telomerase activity, said method comprising providing a sample of nucleic acid substrate for telomerase; contacting said sample with a molecule as described above; monitoring the binding of said molecule to said nucleic acid sample; contacting said nucleic acid sample with a telomerase; contacting said nucleic acid sample with a molecule as described above; monitoring the binding of said molecule to said telomerase treated nucleic acid sample, and comparing the binding of the first monitoring step with the binding of the second monitoring step.

This or other aspect(s) may comprise dispensing a nucleic acid sample into the wells of a plate suitable for use with an ELISA reader such as a 96-well microtitre plate. Gq1* labelled with fluorescent dye or enzyme is then added to the well, incubated and washed, and the binding of the Gq1* molecules to the nucleic acid sample is measured by fluorescence or ELISA. The telomerase or candidate telomerase is added to the nucleic acid sample, and incubated at a suitable temperature for the telomerase or candidate telomerase to function. Fresh Gq1* labelled with fluorescent dye or enzyme is then added to the well, incubated and washed, and the binding of the Gq1* molecules to the nucleic acid sample is measured by fluorescence or ELISA. The binding of the Gq1* molecules according to the invention to the nucleic acid sample before and after treatment with the telomerase or candidate telomerase is compared. A higher binding coefficient after telomerase treatment indicates that more target nucleic acid is present after telomerase treatment, and thus indicates that telomerase activity was indeed present in the sample. This method can be easily adapted for estimating the length of telomere(s), by simply measuring the binding of an excess of molecules according to the invention to normalised masses of nucleic acid sample. The amount of bound molecule per given mass of DNA then provides an estimate of the length of the telomere (s), if any are present.

Thus, in another aspect, the invention relates to a method for estimating the length of telomere(s), said method comprising contacting said telomere(s) with a molecule as described above; monitoring the binding of said molecule to said telomere sample, and estimating the length of said telomeres from the strength of said binding.

In another aspect, the invention relates to a method for assaying telomerase activity, said method comprising; providing a sample of nucleic acid substrate for telomerase; contacting said nucleic acid sample with a telomerase; contacting said nucleic acid sample with a molecule as described above, and monitoring the binding of said molecule to said telomerase treated nucleic acid sample. This is discussed in more detail below, such ,is in the Examples section.

In another aspect, the invention relates to a method for discriminating between duplex and quadruplex nucleic acid comprising contacting a sample of nucleic acid with a molecule as described above, and monitoring the binding of said molecule to said nucleic acid. 'Discriminating between' means that the two or more entities which are being discriminated may be told apart or mutually excluded or identified or otherwise distinguished. In this example, the term is used to mean that duplex nucleic acid and quadruplex nucleic acid may be distinguished using this method.

In another aspect. the invention relates to a method for detecting telomeric structures in vivo comprising contacting a labelled molecule as described above with a sample, and monitoring said labelled molecule. The molecule may be labelled using any suitable method as are well known in the art and include fluorescent labelling, radioactive labelling, peptide tagging, immunolabelling and the like. These are discussed in more detail below.

In another aspect, the invention relates to a method for manipulating telomeric structure(s) in vivo comprising contacting a labelled molecule as described above with a telomeric structure, wherein said molecule further comprises an effector domain. In this context, 'manipulating' means altering, binding, cleaving, modifying (such as chemical and/or enzymatic modification) or similar effect. An effector domain may be a repressor domain, a nuclease, a tag, an enzyme or enzymatic activity, a toxin, a prodrug or any other suitable effector as discussed below.

In another embodiment, the present invention relates to the design and selection of zinc fingers that bind single stranded telomeric DNA in the G-quadruplex conformation.

In another aspect, the invention relates to a method as described above wherein said assay method comprises an ELISA assay.

In another aspect, the invention relates to a method as described above wherein said assay method is in micro-well format.

DETAILED DESCRIPTION OF THE INVENTION

The term "library" is used according to its common usage in the art, to denote a collection of polypeptides or, preferably, nucleic acids encoding polypeptides. The polypeptides of the invention contain regions of randomisation, such that each library will comprise or encode a repertoire of polypeptides, wherein individual polypeptides differ in sequence from each other. The same principle is present in virtually all libraries developed for selection, such as by phage display.

Randomisation, as used herein, refers to the variation of the sequence of the polypeptides which comprise the library, such that various amino acids may be present at any given position in different polypeptides. Randomisation may be complete. such that any amino acid may be present at a given position, or partial, such that only certain amino acids are present. Preferably, the randomisation is achieved by mutagenesis at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

Variants

The nucleic acid binding polypeptide molecule as provided by the present invention includes splice variants encoded by mRNA generated by alternative splicing of a primary transcript, amino acid mutants, glycosylation variants and other covalent derivatives of said molecule which retain the physiological and/or physical properties of said molecule, such as its nucleic acid binding activity. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope, or may be a molecule capable of facilitating crossing of cell membrane(s) etc.

Derivatives can be fragments of the nucleic acid binding molecule. Fragments of said molecule comprise individual domains thereof, as well as smaller polypeptides derived from the domains. Preferably, smaller polypeptides derived from the molecule according to the invention define a single epitope which is characteristic of said molecule. Fragments may in theory be almost any size, as long as they retain one characteristic of the nucleic acid binding molecule. Preferably, fragments may be at least 3 amino acids and in length.

Derivatives of the nucleic acid binding molecule also comprise mutants thereof, which may contain amino acid deletions, additions or substitutions, subject to the requirement to maintain at least one feature characteristic of said molecule. Thus, conservative amino acid substitutions may be made substantially without altering the nature of the molecule, as may truncations from the N- or C- terminal ends, or the corresponding 5'- or 3'- ends of a nucleic acid encoding it. Deletions or substitutions may moreover be made to the fragments of the molecule comprised by the invention. Nucleic acid binding molecule mutants may be produced from a DNA encoding a transcription protein which has been subjected to in vitro mutagenesis resulting e.g. in an addition, exchange and/or deletion of one or more amino acids. For example, substitutional, deletional or insertional variants of the molecule can be prepared by recombinant methods and screened for nucleic acid binding activity as described herein.

The fragments, mutants and other derivatives of the polypeptide nucleic acid binding molecule preferably retain substantial homology with said molecule. As used herein. "homology" means that the two entities share sufficient characteristics for the skilled person to determine that they are similar in origin and/or function. Preferably, homology is used to refer to sequence identity. Thus, the derivatives of the molecule preferably retain substantial sequence identity with the sequence of said molecule.

"Substantial homology", where homology indicates sequence identity, means more than 75% sequence identity and most preferably a sequence identity of 90% or more. Amino acid sequence identity may be assessed by any suitable means, including the BLAST comparison technique which is well known in the art, and is described in Ausubel et al., Short Protocols in Molecular Biology (1999) $4^{th}$ Ed, John Wiley & Sons, Inc.

Mutations

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990) Preferably, the commercially available Altered Site 11 Mutagenesis System (Promega) may be employed, according to the directions given by the manufacturer.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pal of bacteriophage ml3 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431–436; Smith, (1985) Science 228:1315–1317; and McCafferty et al., (1990) Nature 348:552–554; all incorporated herein by reference. Vector systems and kits for phage display are available commercially, for example from Pharmacia.

The present invention allows the production of what are essentially artificial nucleic acid binding proteins. In these proteins, artificial analogues of amino acids may be used, to impart the proteins with desired properties or for other reasons. Thus the term "amino acid", particularly in the context where "any amino acid" is referred to means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues of the defined amino acids.

Molecules according to the invention are preferably zinc finger polypeptides. In other words, they comprise a Cys2-His2 zinc finger motif.

Zinc Fingers

A zinc finger is a DNA-binding protein domain that may be used as a scaffold to design DNA-binding proteins with predetermined sequence-specificity (Klug, A. & Rhodes, D. (1987) 'Zinc fingers': a novel protein motif for nucleic acid recognition. *Trends Biochem. Sci.* 12, 464–469; Choo, Y. & Klug, A. (1995) Designing DNA-binding proteins on the surface of filamentous phage. *Curr. Opin. Biotech.* 6, 431–436). The peptide motif comprises about 30 amino acids that adopt a compact DNA-binding structure on chelating a zinc ion (Miller, J., McLachlan, A. D. & Klug, A. (1985) Repetitive zinc-binding domains in the protein transcription factor IIIA from *Xenopus oocytes*. *EMBO J* 4, 1609–1614). Each zinc finger module is capable of recognising 3–4 bp of DNA, such that arrays comprising tandemly repeated modules bind proportionally longer nucleotide sequences. The crystal structure of the Zif268 DNA-binding domain, in complex with its optimal DNA binding site, shows that the zinc finger array wraps around the DNA, with the a-helix of each finger buried in the major groove (Pavletich, N. P. & Pabo, C. O. (1991) Zinc finger-DNA recognition: Crystal structure of a Zif268-DNA complex at 2.1 Å. *Science* 252, 809–817).

The geometrical properties of zinc finger structures mean that a versatile binding surface can be created by varying a small number of amino acid positions on each finger's central α-helix. Moreover, zinc fingers may be linked together to bind to longer, contiguous stretches of DNA. Large randomised libraries of zinc fingers have been engineered by phage display, so that zinc finger variants are displayed on the viral capsid. Such libraries have been extensively screened to select fingers that bind to various duplex DNA sequences (Choo, Y., & Klug, A. (1994) *Proc. Natl. Acad Sci. U.S.A.* 91, 11163–11167. Greisman, H. A., & Pabo, C. O. (1997) *Science* 275. 657–661. Jamieson, A. C., Kim, S.-H., & Wells, J. A. (1994) *Biochemistry* 33, 5689–5695. Wu, H., Yang, W.-P., & Barbas III, C. F. (1995) *Proc. Natl. Acad Sci. USA* 92, 344–348. Isalan, M., Klug, A., & Choo, Y. (1998) *Biochemistry* 37, 12026–12033.)and to RNA (Friesen, W. J., & Darby, M. K. (1997) *J Biol Chem* 272, 10994–10997. Friesen, W. J., & Darby, M. K. (1998) *Nat Struct Biol* 5, 543–546. Blancafort, P., Steinberg, S. V., Paquin, B., Klinck, R., Scott, J. K., & Cedergren, R. (1999) *Chemistry and Biology* 6, 585–597.).

Zinc fingers, as is known in the art, are nucleic acid binding molecules. A zinc finger binding motif is a structure well known to those in the art and defined in, for example, Miller et al., (1985) EMBO J. 4:1609–1614; Berg (1988) PNAS (USA) 85:99–102; Lee et al., (1989) Science 245:635–637; see International patent applications WO 96/06166 and WO 96/32475, corresponding to U.S. Ser. No. 08/422,107, incorporated herein by reference.

As used herein, "nucleic acid" refers to both RNA and DNA, constructed from natural nucleic acid bases or synthetic bases, or mixtures thereof. Preferably, however, the binding proteins of the invention are DNA binding proteins.

All of the nucleic acid-binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Cys2-His2 zinc finger binding proteins, as is well known in the art, bind to target nucleic acid sequences via α-helical zinc finger metal atom co-ordinated binding motifs known as zinc fingers.

These and other considerations may be incorporated in a library set in accordance with the invention.

Vectors

The nucleic acid encoding the nucleic acid binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be a transformed with the vector. Each vector contains various components depending on its function (amplification of DNA or expression of DNA) and the host cell for which it is compatible. The vector components generally include, hut are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors. this sequence is one that enables the vector to replicate independently of thee host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding the nucleic acid binding protein is more complex than that of exogenously replicated vector because restriction enzyme digestion is required to excise nucleic acid binding protein DNA. DNA can be amplified by PCR and be directly transfected into the host cells without any replication component.

Selectable Markers

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are. for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the nucleic acid binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression

Expression and cloning vectors usually contain a promoter that is recognised by the host organism and is operably linked to nucleic acid binding protein encoding nucleic acid. Such a promoter may be inducible or constitutive. The promoters are operably linked to DNA encoding the nucleic acid binding protein by removing the promoter from the source DNA by restriction enzyme digestion and inserting the isolated promoter sequence into the vector. Both the native nucleic acid binding protein promoter sequence and many heterologous promoters may be used to direct amplification and/or expression of nucleic acid binding protein encoding DNA.

Promoters suitable for use with prokaryotic hosts include, for example, the β-lactamase and lactose promoter systems, alkaline phosphatase, the tryptophan (Trp) promoter system and hybrid promoters such as the tac promoter. Their nucleotide sequences have been published, thereby enabling the skilled worker operably to ligate them to DNA encoding nucleic acid binding protein, using linkers or adapters to supply any required restriction sites. Promoters for use in bacterial systems will also generally contain a Shine-Delgarno sequence operably linked to the DNA encoding the nucleic acid binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the *E. coli* BL21 (DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpressTm (Invitrogen) or pTrc99 (Pharmacia Biotech, SE) or vectors containing the tac promoter such as pKK223-3 (Pharmnacia Biotech) or PMAL (New England Biolabs, MA., USA).

Moreover, the nucleic acid binding protein molecule according to the invention preferably includes a secretion sequence in order to facilitate secretion of the polypeptide from bacterial lists, such that it will be produced as a soluble native peptide rather than in an inclusion body. The peptide may be recovered from the bacterial periplasmic space, or the culture medium, as appropriate. A "leader" peptide may be added to the N-terminal finger. Preferably, the leader peptide is MAEEKP.

Suitable promoting sequences for use with yeast hosts may be regulated or constitutive and are preferably derived from a highly expressed yeast gene, especially a Saccharomyces cerevisiae gene. Thus, the promoter of the TRP1 gene, the ADHI or ADHII gene. the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosplioglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene. for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such is the PH05 (−173) promoter element starting at nucleotide −173 and ending at nucleotide −9 of the PH05 gene.

Nucleic acid binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with nucleic acid binding protein sequence, provided such promoters are compatible with the host cell systems.

Transcription of a DNA encoding nucleic acid binding protein by higher cukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 540 or 3' to nucleic acid binding protein DNA, but is preferably located at a site 5' from the promoter.

Advantageously, a eukaryotic expression vector encoding a nucleic acid binding protein according to the invention may comprise a locus control region (LCR) LCRs are capable of directing high-level integration site independent expression of transgenes integrated into host cell chromatin, which is of importance especially where the nucleic acid binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and or stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding nucleic acid binding protein.

An expression vector includes any vector capable of expressing nucleic acid binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding protein may be inserted into a vector suitable for expression of cDNAs in mammalian cells, e.g. a CMV enhancer-based vector such as pEVRF (Matthias, et al. (1989) NAR 17,6418).

Particularly useful for practising the present invention are expression vectors that provide for the transient expression of DNA encoding nucleic acid binding protein in mammalian cells. Transient expression usually involves the use of an expression vector that is able to replicate efficiently in a host cell, such that tile host cell accumulates many copies of the expression vector. and, in turn, synthesises high levels of nucleic acid binding protein. For the purposes of the present invention, transient expression systems are useful e.g. for identifying nucleic acid binding protein mutants, to identity potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts. introducing DNA into host cells, and performing analyses for assessing nucleic acid binding protein expression and function are known to those skilled in the art. Gene presence amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher cukaryote cells may be used for replicating DNA and producing the nucleic acid binding protein. Suitable prokaryotes include eubacteria, such as Gram-negative or Gram-positive organisms, such as E. coli, e.g. E. coli K-12 strains, DH5a and HB101, or Bacilli. Further hosts suitable for the nucleic acid binding protein encoding vectors include eukaryotic microbes such as filamentous fungi or yeast, e.g. Saccharomyces cerevisiae. Higher eukaryotic cells include insect and vertebrate cells, particularly mammalian cells including human cells or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CIIO) cells, NIII 3T3 cells. HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells. the cells should be transfected with a sufficient amount of the nucleic acid binding protein-encoding nucleic acid to form the nucleic acid binding protein. The precise amounts of DNA encoding the nucleic acid binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the nucleic acid binding protein encoded by the DNA is expressed. The composition of suitable media is known to those in the art, so that they can be readily prepared. Suitable culturing media are also commercially available.

Nucleic acid binding molecules according to the invention may be employed in a wide variety of applications, including diagnostics and as research tools. Advantageously, they may be employed as diagnostic tools for identifying the presence of nucleic acid molecules in a complex mixture.

Zinc finger domains may be made by methods described and/or referred to herein. For example, said zinc finger DNA binding domains may be made as discussed in the examples, or as described in one or more of WO96/06166, WO98/53058, WO98/53057, or WO/98/53060.

Telomeres, G-quadruplexes and G-quartets

Telomeres comprise highly conserved DNA repeat sequences, associated with proteins, found at the ends of chromosomes in nearly all eukaryotes. They are widely studied because of their important roles in maintaining chromosome stability and in mediating normal chromosome segregation in mitosis and meiosis (Rhodes. D., & (Giraldo, R. (1995) *Curr Opin Str Biol* 5, 311–322.).

Because of their potential importance, G-quadruplexes have been extensively characterised in terms of structure, polymorphism, ion selectivity, stability and folding kinetics [reviewed in (Williamson, J. R. (1994) *Annual Review Of Biophysics and Biomolecular Structure* 23, 703–730.)].

Telomeric DNA sequences contain characteristic guanine-rich repeats of the form $d(T_{1-3}-(T/A)-G_{3-4})_n$ [reviewed in (Blackburn, E. H., & Szostak, J. W. (1984) *Annual Review Of Biochemistry* 53, 163–194.)]. These sequences form G-quadruplex secondary structures in vitro at physiological salt concentrations ($K^+$ or $Na^+$) and it has been proposed that such structures may be of biological significance in vivo. It has been suggested that inter-telomeric G-quadruplexes may determine the correct association of homologous chromosomes in different stages of the cell cycle (Sen, D., & Gilbert, W. (1988) *Nature* 334, 364–366. Sundquist, W. I., & Klug. A. (1989) *Nature* 342, 825–829. Williamson, J. R., Raghuraman, M. K., & Cech, T. R. (1989) *Cell* 59, 871–880.). More recently, it has been suggested that the G-quadruplex conformation of single stranded telomeric DNA may be important to the mechanism and regulation of telomerase-mediated telomere extension (Salazar M, Thompson B D, Kerwin S M, Hurley L H. (1996) *Biochemistry* 35(50):16110–5. Sun. D., LopezGuajardo, C. C., Quada, J., Hurley, L. H., & VonHoff, D. D. (1999) *Biochemistry* 38, 4037–4044.). Furthermore, G-quadruplexes have emerged as a molecular target for therapeutics particularly in cancer research (Sun D, Thompson 13, Cathers B E, Salazar M, Kerwin S M, Trent J O, Jenkins T C, Neidle S, Hurley L H (1997) *J Med Chem* Jul 4;40(14):2113–6. Perry P J, Reszka A P, Wood A A. Read M A. Gowan S M, Dosanjh H S, Trent J O, Jenkins T C, Kelland L R, Neidle S. (1998) *J. Med Chem.* 41(24):4873–84.).

Several naturally occurring proteins with affinity for G-quadruplexes have been reported (Wellinger, R. J., & Sen, D. (1997) *European Journal of Cancer* 33, 735–749.), although there are problems associated with their use as diagnostic or therapeutic probes. Most examples, such as a recently reported DNA-binding autoantibody (Brown, B. A., Li, Y. Q., Brown, J. C., Hardin, C. C., Roberts, J. F., Pelsue, S. C. & Shultz, L. D. (1998) *Biochemistry* 37, 16325–16337.), have only moderate binding affinities and discriminate weakly between duplex and quadruplex DNA. Naturally occurring high-affinity telomere-binding proteins also appear unable to discriminate these structures. For example. *Saccharomyces cerevisiae* RAP1 (Giraldo, R., & Rhodes, D. (1994) *EMBO J* 13, 2411–2420.) has distinct but inseparable domains for binding quadruplexes and double stranded DNA.

Prior art telomere-binding proteins have only moderate binding affinities and/or discriminate weakly between duplex and quadruplex DNA.

The molecules of the present invention may be used as probes for the presence of G-quadruplex structures, both it vitro and in vivo.

The the present invention facilitates ELISA-based detection of telomerase activity. This detection system is rapid, easily automated with liquid handling robotics and avoids the need to use radioactivity. This contrasts with prior art telomerase assays such as the commercially-available 'TRAP' assay.

Telomere-binding molecules according to the present invention may be used to target chromosome ends and deliver effector activity, for example using fusions with other peptides or enzymes.

It is envisaged that the present invention may be of use in diverse areas, including for example one or more of the following; diagnostics, assays, elisa testing, probe production, genomics studies such as pharmacogenomics, therapeutic applications such as study or construction of disease model(s), drug design, peptide/protein research, the construction or exploitation of research tools such as molecular marker(s) and similar reagents, as well as use in screening such as using chip technology. cellular or in vitro assay(s), molecular detection as well as target identification or validation.

The present invention may also be of use in the study and/or treatment of metabolic disorders, or cancer.

The present invention facilitates the construction of ELISA-based diagnostic kits for the detection of telomerase activity. These assays are rapid, easily automated with liquid handling robotics and avoid the need to use radioactivity. in contrast to prior art technologies such as the 'TRAP' assay.

The present invention encompasses the development of probes for examining G-quartet formation in vivo.

Telomere-binding molecules according to the invention may be used to target chromosome ends and to deliver effector activity in the form of fusions with other peptides or enzymes. Therapeutic applications of the invention include those associated with the role(s) of telomeres in ageing and/or cancer.

Telomere-binding molecules according to the invention may affect telomerase activity and may be used as, or in conjunction with, inhibitors of this enzyme, the activity of which is associated with cell immortalisation and cancer.

Zinc finger protein molecules according to the invention may be selected from a phage display library to bind G-quadruplex DNA structures of single stranded human telomeric sequences with selectivity and high affinity. Advantageously, these zinc fingers have no detectable affinity for a duplex DNA made up of the Htelo sequence and its complementary strand. These molecules represent a new class of DNA-binding zinc fingers and have utility for both study and exploration of the molecules themselves, and of therapeutics and assays, in addition to their utility as in vitro or in vivo molecular probes to explore possible mechanisms of inhibition and regulation of telomerase-mediated telomere extension. The widespread conservation G-quadruplex-forming sequences at chromosome ends means that the molecules according to the invention will find utility in a wide range of biological systems.

Since in vitro diagnostic methods for detecting G-quadruplexes, such as circular dichroism (Giraldo, R., Suzuki, M., Chapman, L., & Rhodes, D. (1994) *Proc Natl Acad Sci* 91, 7658–7662.) and dimethyl sulphale protection (Sen, D., & Gilbert, W. (1992) *Methods In Enzymology* 211, 191–199.), cannot be carried out in living cells. the invention is useful in relation to derivatives (e.g. fluorescent derivatives) of these zinc fingers which may reveal the presence, location and relevance of these telomeric structures in vivo.

Molecules according to the present invention are useful in the binding of non-conventional nucleic acid structures.

Examples of such structures include non-Watson-Crick base paired DNA, for example Hoogsteen base paired DNA or other variants. Furthermore, non-conventional DNA structures include non-double helical DNA conformations.

Fusions

According to a further aspect, the invention provides a nucleic acid binding polypeptide capable of binding to telomeric, G-quadruplex or G-quartet nucleic acid wherein said polypeptide comprises a nucleic acid binding domain and one or more further domain(s) joined thereto. Said domains may be joined by any suitable means known in the art, such as by conjugation, fusion, or other suitable method. Preferably, said domains are comprised by a single polypeptide fusion protein. Such a nucleic acid binding polypeptide may comprise nucleic acid binding domains linked by at least one flexible linker, one or more domains linked by at least one structured linker, or both.

According to a further aspect, the invention provides a nucleic acid binding polypeptide comprising a repressor domain and one or more nucleic acid binding domains. The repressor domain is preferably a transcriptional repressor domain selected from the group consisting of: a KRAB-A domain, an engrailed domain and a snag domain.

The nucleic acid binding polypeptides according to our invention may be linked to one or more transcriptional effector domains, such as an activation domain or a repressor domain. Examples of transcriptional activation domains include the VP16 and VP64 transactivation domains of Herpes Simplex Virus. Alternative transactivation domains are various and include the maize C1 transactivation domain sequence (Sainz et al., 1997, Mol. Cell. Biol. 17: 115–22) and P1 (Goff et al., 1992, Genes Dev. 6: 864–75; Estruch et al., 1994, Nucleic Acids Res. 22: 3983–89) and a number of other domains that have been reported from plants (see Estruch et al., 1994, ibid).

Instead of incorporating a transactivator of gene expression, a repressor of gene expression can be fused to the nucleic acid binding polypeptide and used to down regulate the expression of a gene contiguous or incorporating the nucleic acid binding polypeptide target sequence. Such repressors are known in the art and include, for example, the KRAB-A domain (Moosmann et al., Biol. Chem. 378: 669–677 (1997)), the KRAB domain from human KOX1 protein (Margolin et al., PNAS 91:4509–4513 (1994)), the engrailed domain (Han et al., Embo J. 12: 2723–2733 (1993)) and the snag domain (Grimes et al., Mol Cell. Biol. 16: 6263–6272 (1996)). These can be used alone or in combination to down-regulate gene expression.

Molecules according to the invention comprising zinc finger proteins may be fused to transcriptional repression domains such as the Kruppel-associated box (KRAB) domain to form powerful repressors. These fusions are known to repress expression of a reporter gene even when bound to sites a few kilobase pairs upstream from the promoter of the gene (Margolin et al., 1994, PNAS USA 91, 4509–4513).

Nucleic acid binding molecules according to the invention may comprise tag sequences to facilitate studies and/or preparation of such molecules. Tag sequences may include flag-tag, myc-tag, 6his-tag or any other suitable tag known in the art.

Advantageously, molecules according to the invention may be used in combination. Use in combination includes both fusion of molecules into a single polypeptide as well as use of two or more discrete polypeptide molecules in solution.

The invention thus relates to the manipulation of telomeric structures using zinc finger peptides and derivative fusion proteins according to the invention. Examples of such manipulation include simple binding, modification eg. methylation, cleavage eg. by nuclease action, or other chemical or physical modification.

Further fusion proteins according to the invention are described herein, for example in the following section.

Pharmaceuticals

Moreover, the invention provides therapeutic agents and methods of therapy involving use of nucleic acid binding proteins as described herein. In particular, the invention provides the use of polypeptide fusions comprising an integrase, such as a viral integrase, and a nucleic acid binding protein according to the invention to target nucleic acid sequences in vivo (Bushman, (1994) PNAS (USA) 91:9233–9237). In gene therapy applications, the method may be applied to the delivery of functional genes into defective genes, or the delivery of nonsense nucleic acid in order to disrupt undesired nucleic acid. Alternatively, genes may be delivered to known, repetitive stretches of nucleic acid, such as centromeres, together with an activating sequence such as an LCR. This would represent a route to the safe and predictable incorporation of nucleic acid into the genome.

In conventional therapeutic applications, nucleic acid binding proteins according to the invention may be used to specifically knock out cell having mutant vital proteins. For example, if cells with mutant ras are targeted, they will be destroyed because ras is essential to cellular survival. Alternatively, the action of transcription factors may be modulated, preferably reduced, by administering to the cell agents which bind to the binding site specific for the transcription factor. For example, the activity of HIV tat may be reduced by binding proteins specific for HIV TAR.

Moreover, binding proteins according to the invention may be coupled to toxic molecules, such as nucleases, which are capable of causing irreversible nucleic acid damage and cell death. Such nucleases include restriction endonuclease domains, non-specific nucleases such as DNAse, RNAse or similar enzymatic activities. Such agents are capable of selectively destroying cells which comprise a mutation in their endogenous nucleic acid.

Nucleic acid binding proteins and derivatives thereof as set forth above may also be applied to the treatment of infections and the like in the form of organism-specific antibiotic or antiviral drugs. In such applications, the binding proteins may be coupled to a nuclease or other nuclear toxin and targeted specifically to the nucleic acids of microorganisms.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilising processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, coin, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate. and/or polyethylene glycol. Sugar-coated tablet cores are provided with suitable coatings which, if desired, are resistant to gastric juice, using, inter alia, concentrated sugar solutions which, if desired, contain Sum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example to identify or to indicate different doses of active ingredient, may be added to the tablets or sugar-coated tablet coatings.

Other orally utilisable pharmaceutical preparations are hard gelatin capsules, and also soft closed capsules made of gelatin and a plasticiser, such as glycerol or sorbitol. The hard gelatin capsules may contain the active ingredient in the form of granules, for example in a mixture with fillers, such as lactose. binders, such as starches, and/or lubricants, such as talc or magnesium stearate, and, if desired, stabilisers. In soft capsules, the active ingredient is preferably dissolved or suspended in suitable liquids. such as fatty oils, paraffin oil or liquid polyethylene glycols, it also being possible to add stabilisers.

Suitable rectally utilisable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, it necessary, also stabilisers.

The dose of the active ingredient depends on the warm-blooded animal species. the age and the individual condition and on the manner of administration. In the normal case, an approximate daily dose of about 10 mg to about 250 mg is to be estimated in the case of oral administration for a patient weighing approximately 75 kg .

The present invention has advantages over existing technology which include but are not limited to increased speed and sensitivity when using amplifying ELISA signal, removal of the need for running electrophoretic gels, and alleviation of the need to use radioactive labelling. Furthermore, the systems of the present invention can be advantageously automated using liquid-handling robotics, resulting in high efficiency and labour-saving.

Without wishing to be bound by theory, the nature of the zinc finger-G-quadruplex interactions is likely to be quite distinct from known zinc finger-duplex DNA interactions.

The invention will now be described by way of Example, with reference to the following figures:

BRIEF DESCRIPTION OF THE FIGURES

FIG. 7 shows Table 1 which shows apparent ELISA dissociation constants ($Kd^E$) of the phage-displayed zinc finger peptide, Gq1, for variants of the Htelo DNA sequence (SEQ ID NOS: 1 and 21–23 and 1, respectively in order of appearance). ELISAs from which binding is too low to determine Kd are denoted by a dash (-).

EXAMPLES

Example 1

Production of Molecules Binding G-quadruplex Structures

Figures 1A, 1B:
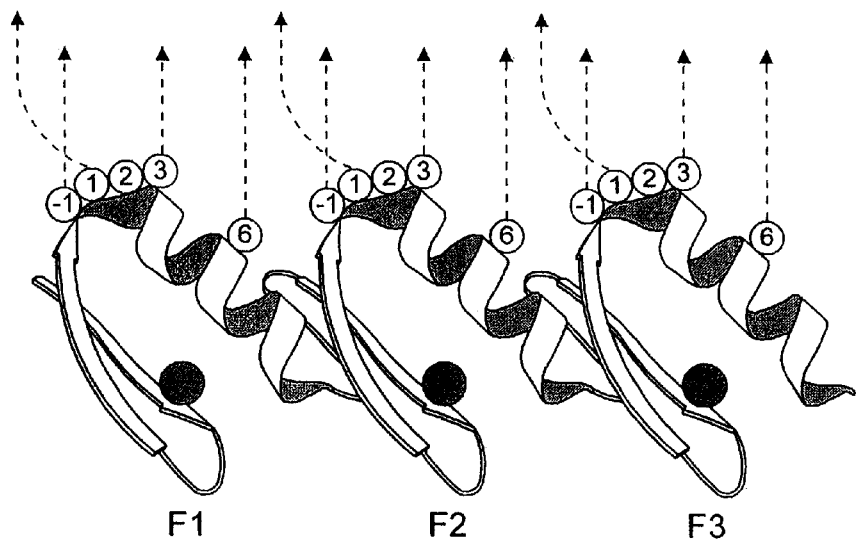
FIG. 1a shows schematic representation of the Zif268 DNA-binding domain, indicating its three zinc finger helices (F1, F2 and F3). The circled numbers represent the key amino acid residues that interact with duplex DNA (relative to the first position of the α-helix, position +1).
FIG. 1b shows amino acids included in the phage display library used in this study. Amino acid residues in the helical regions of fingers 1–3 (F1–F3) are shown in single letter code, numbered relative to the first helical position (position 1). Note that library construction involved cloning a subset of the possible combinations shown above, although these clones were pre-enriched for DNA-binding potential (See below).

In this Example, DNA-binding proteins of the zinc finger family are engineered to bind specifically to a telomeric (i-quadruplex nucleic acid structure.

A zinc finger library is screened for molecules that bind to an oligonucleotide containing the human telomeric repeat sequence in the G-quadruplex conformation. The selected molecular clones exhibit amino acid homologies (consensus sequences). Without wishing to be bound by theory, this suggests that the molecules have analogous modes of binding. Binding is both sequence-dependent and structure-specific. This is the first example of a designed molecule that binds to G-quadruplex DNA. Further, this represents a new type of binding interaction for a zinc finger protein molecule.

G-quadruplex DNA Ligand Preparation

It has been previously reported that the human telomeric sequence (5'-GTTAGG-3')n forms G-quadruplex structures in vitro (Balagurumoorthy, P., Brahmachari, S. K., Mohanty, D., Bansal, M., & Sasisekharan, V. (1992) *Nucleic Acids Research* 20. 4061–4067. Balagurumoorthy, P., & Brahmachari, S. K. (1994) *Journal of Biological Chemistry* 269, 21858–21869. Fletcher, T. M., Sun, D. K., Salazar, M., & Hurley, L. H. (1998) *Biochemistry* 37, 5536–5541.). The five repeat telomeric oligonucleotide sequence (SEQ ID NO: 24) (5'-GTTAGG-3')5 (Htelo) is employed as the ligand for affinity selection of phage herein.

Syntesised oligonucleotides (Oswel Ltd.) are purified by fractionation in denaturing polyacrylamide-urea gels, recovered by elution and desalted further using Waters sep-Pack C-18 cartridges with final elution in 25 mM Tris, pH 7.5 as described by Giraldo et al. (Giraldo, R., & Rhodes, D. (1994) *EMBO J* 13, 241 1–2420.).

The sequence (SEQ ID NO: 1) 5'-biotin-GGTTAG GGT-TAG GGTTAG GGTTAG GGTTAG-3'('Biotin-Htelo') is prepared for the phage selection experiments and the unbiotinylated sequence ('Htelo') is used for gel mobility shift and DMS protection experiments.

Oligonucleotides are then annealed for quadruplex formation, and subsequently used for ELISA and/or gel assays (see below). Oligonucleotides are diluted to 10 pmol/µl in 25 mM Tris (pH 7.5) or phosphate-buffered KCl or NaCl (pH 7.5) with cation concentrations ranging from 25 mM to 150 mM. Annealing or quadruplex formation is carried out by heating samples to 95° C. on a thermal heating block, and cooling to 4° C. at a rate of 2° C./min. The double stranded DNA (ds Htelo) is made by primer extension with the Klenow fragment of DNA polymerase.

Structures formed by human telomeric sequences may be analysed using dimethyl sulphate protection analysis to determine the existence of G-quadruplexes therein. To confirm that Htelo is folded into a G-quadruplex in the presence of sodium and potassium ions, a dimethyl sulphate (DMS) protection assay is carried out (Sundquist, W. I., & Klug, A. (1989) *Nature* 342, 825–829.). G-quadruplex formation involves Hoogsteen-type base pairing of guanines which protects N-7 of guanine against methylation on exposure to the potent methylating agent DMS. Subsequent cleavage of the DNA backbone at methylated guanines can be mediated by heating in aqueous piperidine (Maxam, A. M., & Gilbert, W. (1980) *Methods Enzymol.* 65, 499–560.).

Figure 2A:
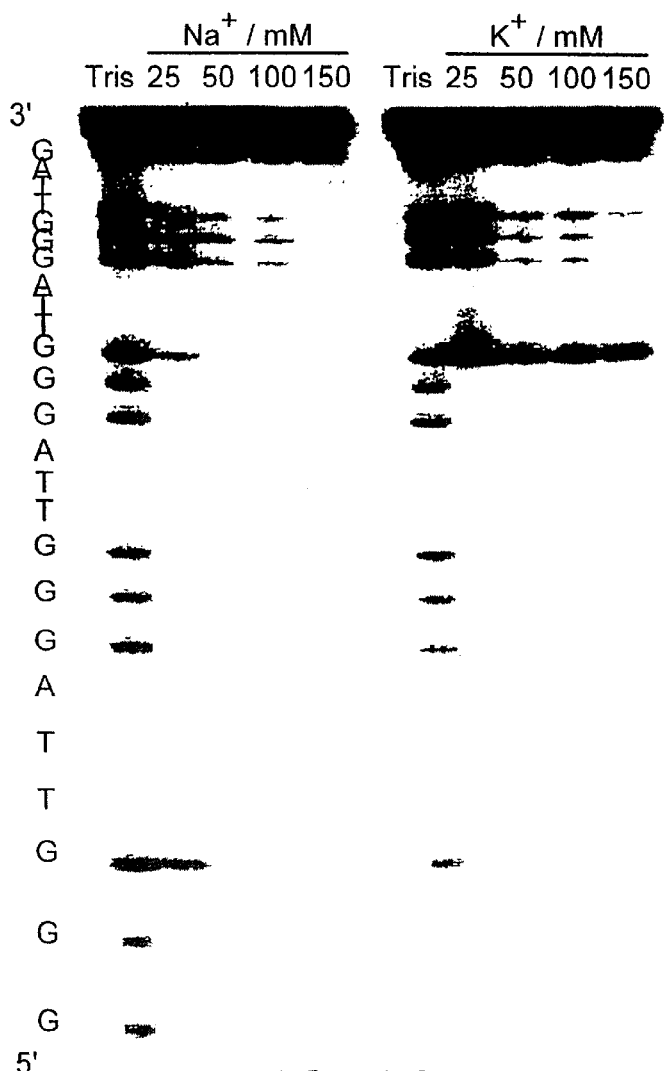
FIG. 2a shows DMS methylation protection analysis of Htelo (SEQ ID NO: 5). End-labelled $^{32}$P-litelo was annealed in KCl or NaCl at the indicated concentrations. Each sample was incubated with DMS for 5 minutes and then cleaved with piperidine. Methylation protection patterns, indicative of G-quadruplex formation, appear after resolution of the cleaved fragments on a 20% polyacrylamide gel. The Tris control lane indicates the reference (non-quadruplex) methylation cleavage pattern of Htelo in the absence of $Na^+$ or $K^+$.
Figure 2B:
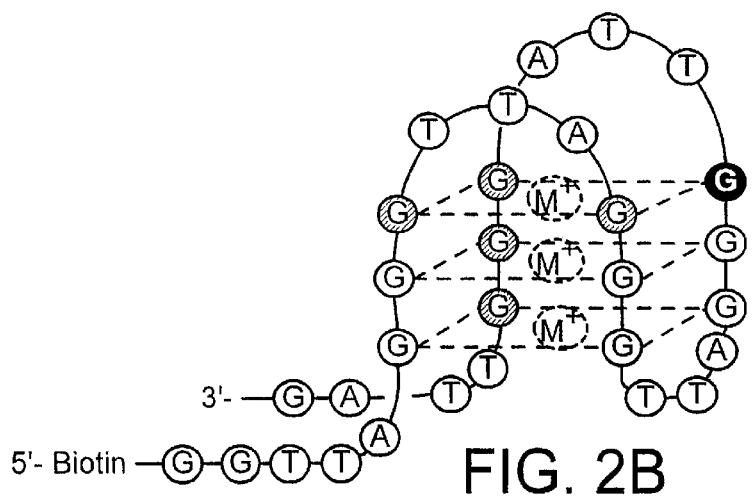
FIG. 2b shows schematic representation of an exemplary isoform of an intramolecular antiparallel G-quadruplex formed by Htelo (SEQ ID NO: 1). Guanines in the G-quartet core are labelled in shaded circles with darker shading indicating a relatively higher amount of cleavage, as observed in the DMS methylation protection analysis. (Note that the structure shown is only one possible isoform and that other 'semi-parallel' conformation(s) such as one comprising a pair of parallel 'up' strands, facing a pair of parallel 'down' strands created by 'crossing-over' of the two top 'TTA' sequences in the figure may also be stable form(s) of Htelo.)

The resulting gel pattern (see for example FIG. 2a) clearly shows that the critical guanines of Htelo are almost completely protected from cleavage, at $K^+$ or $Na^1$ concentrations above 100 mM, as compared to a Tris-HCl buffer control. Non-denaturing gels confirm that these folded forms are of a single species and therefore antiparallel intramolecular G-quadruplexes, ie. similar to the structure illustrated in FIG. 2b. Intermolecular G-quadruplexes are not observed in detectable amounts under these conditions. Without wishing to be bound by theory, this is probably because of their slow folding kinetics and/or because of the relatively low concentrations of DNA used which are likely to promote intramolecular G-quadruplex formation (Hardin C C, Henderson E, Watson T, Prosser J K (1991) *Biochemistry* May 7;30(18):4460–72).

A zinc finger phage display library is constructed specifically to select candidates that bind human telomeric DNA sequences, under conditions that promote G-quadruplex formation. The library is made up of zinc fingers with selectively randomised residues, biased for dsDNA binding potential (Choo, Y., & Klug, A. (1994) *Proc. Natl. Acad Sci. U.S.A.* 91, 11163–11167. Isalan, M., Klug, A., & Choo, Y. (1998) *Biochemistry* 37, 12026–12033). Similar libraries have been extensively characterised, both biochemically and structurally, but only in their capacity to bind duplex DNA sequences in the major groove. (Choo, Y., & Klug. A. (1997) *Curr. Opin. Str. Biol.* 7, 117–125. Choo, Y., & Isalan, M. D. (2000) *Current Opinion in Structural Biology* 10).

Because of practicalities of library handling, a complementary sub-library strategy is employed. Consequently, two complete sub-libraries are constructed and enriched for DNA-binding potential by selection against randomised dsDNA sequences (see below). The resulting clones are recombined ion vitro to make a library containing randomisations over all three fingers.

Construction of Phage Display Library

A phage display library is constructed, based on the three-finger DNA-binding domain of Zif268, whose structure is well characterised (Elrod-Erickson, M., Rould, M. A., Nekludova, L., & Pabo, C. O. (1996) *Structure* 4, 1171–1180. Pavletich, N. P., & Pabo, C. O. (1991) *Science* 252, 809–817.).

A zinc finger DNA-binding domain library is constructed comprising the amino acid framework of wild-type Zif268, but containing randomisations in amino acid positions over all three fingers (see FIG. 1). Due to the practicalities of library cloning (ie. working with about ~$10^6$–$10^7$ transformants), the final library is advantageously constructed from two complementary sub-libraries: Sub-library-1 contains randomisations in F1 (−1→6) and F2 (−3→3). Conversely, sub-library-2 contains randomisations in F2 (3→6) and F3 (−1→6). In both sub-libraries, the non-randomised regions retain the wild-type Zif268 framework.

The genes for each sub-library are assembled from synthetic DNA oligonucleotides by directional end-to-end ligation using short complementary DNA linkers. The oligonucleotides contain selectively randomised codons, encoding a subset of the 20 amino acids, in the appropriate positions within the zinc fingers. Assembled constructs are amplified by PCR using primers containing Not I and Sfi I restriction sites, digested with the above endonucleases to produce cloning overhangs, and ligated into similarly prepared vector Fd-Tet-SN (Choo, Y., & Klug, A. (1994) *Proc. Natl. Acad. Sci. U.S.A.* 91, 11163–11167.) Electrocompetent *E. coli* TG1 cells are transformed with the recombinant vector and plated onto TYE medium (1.5% (w/v) agar, 1% (w/v) Bactotryptone, 0.5% (w/v) Bactoyeast extract, 0.8% (w/v) NaCl) containing 15 µg/ml tetracycline.

The sub-libraries are enriched for DNA-binding members by selecting against random DNA-sequences.

The 3-finger phage library is screened with (SEQ ID NO: 1) 5′-biotin-(GGTTAG)5 (Biotin-Htelo) which has been annealed in a phosphate-buffered solution containing 150 mM potassium ions then immobilised on streptavidin tubes. These salt conditions are maintained throughout the selection protocol to help maintain the structural integrity of the G-quadruplex.

Phage selections are performed as follows:

Tetracycline resistant library colonies of *E. coli* TG1 cells are transferred from plates into 2×TY medium (16 g/litre Bactotryptone, 10 g/litre Bactoyeast extract, 5 g/litre NaCl) containing 50 µM ZnCl$_2$ and 15 µg/ml tetracycline, and cultured overnight at 30° C. in a shaking incubator. Cleared culture supernatant containing phage particles is obtained by centrifuging at 300 g for 5 minutes.

For the first rounds of selection, appropriate quantities of biotinylated DNA target site are immobilised on streptavidin-coated tubes (Roche) in 50 µl phosphate buffer (pH 7.4) containing 50 µM ZnCl$_2$ and 150 mM KCl for 30 minutes at room temperature. Bacterial culture supernatant containing phage is diluted 1:10 in selection buffer (phosphate buffer pH 7.4 with 150 mM KCl) containing 50 µM ZnCl$_2$, 2% (w/v) fat-free dried milk (Marvel), 1% (v/v) Tween, 20 µg/ml sonicated salmon sperm DNA), and 1 ml is applied to each tube. After 1 hour at 20° C., the tubes are emptied and washed 20 times with selection buffer containing 50 µM ZnCl$_2$, 2% (w/v) fat-free dried milk (Marvel) and 1% (v/v) Tween.

Retained phage are eluted in 0.1 M triethylamine and neutralised with an equal volume of 1 M Tris-HCl (pH 7.4). Logarithmic-phase *E. coli* TG1 are infected with eluted phage, and cultured overnight at 30° C. in 2×TY medium containing 50 µM ZnCl$_2$ and 15 µg/ml tetracycline, to amplify phage for subsequent rounds of selection.

For enrichment of the sub-libraries 1 and 2, 50 pmol of biotinylated semi-random oligonucleotides of the form (SEQ ID NOS: 2 and 3) 5′-TATANNNNNNNGGCGTGT CACAGTCAGCTTCAACGTC-3′ and 5′-TATGT GCGGNNNNNNNTCACAGTCAGTCCACACGTC-3′, respectively, are used in selection round 1. These amounts are reduced to 20 pmol and 10 pmol in rounds 2 and The heterogeneous genes from the selected clones are recovered by PCR and recombined via a DdeI site, present in the sequence coding for positions +4 and +5 in F2 of both libraries (see WO98/53057). Recombinants are then re-cloned into phage vector, as described above. Ultimately, 3×$10^6$ selection-enriched library members are obtained, containing randomisations over all 3 zinc fingers.

For selections against Biotin-Htelo, using the full recombined library, 100 pmol of the pre-annealed oligonucleotide is immobilised on streptavidin-coated tubes in the first round. In rounds 2 and 3, selection pressure is increased by reducing the amount of target site to 50 pmol and 1 pmol, respectively. In these rounds, 50 pmol of duplex and 50 pmol single stranded competitor oligonucleotides are also added of the form (SEQ ID NO: 4): 5′-TATANNNNNNNNNNNN NTCACAGTCAGTCCACACGTC-3′. After 3 rounds of selection, *E. coli* TG1 infected with selected phage are plated. Individual colonies are picked and used to prepare phage for ELISA assays and DNA sequencing.

After three rounds of selection, four different zinc finger clones are recovered and individually screened for binding to immobilised Biotin-Htelo by an ELISA assay (Choo, Y., & Klug, A. (1994) *Proc. Natl. Acad. Sci. U S.A.* 91, 11163–11167.).

The four isolated clones (Gq1-4) are sequenced. The coding sequence of individual zinc finger clones is amplified by PCR from phage samples. PCR products are sequenced manually using Thermo Sequence cycle sequencing (Amersham Life Science).

Figures 3, 4:
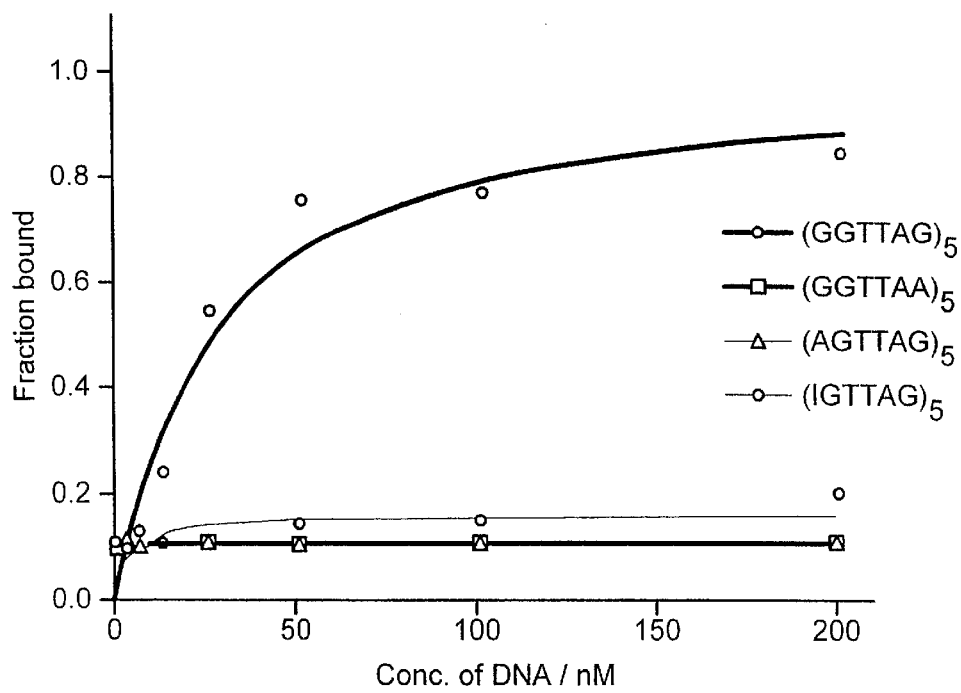
FIG. 3 shows peptide sequences of the zinc finger helical domains of the four proteins Gq1-4 (SEQ ID NOS: 6–17, respectively, in order of appearance), obtained after three rounds of selection. Amino acid residues in fingers 1–3 (F1–F3) are shown in single letter code, numbered relative to the first helical position (position +1). The zinc finger helices of the wild-type Zif268 DNA-binding domain (SEQ ID NOS: 18–20, respectively in order of appearance) are also shown for comparison.
FIG. 4 shows apparent equilibrium binding curves for protein Gq1 binding to single-stranded DNA sequences (SEQ ID NOS: 1 and 21–23, respectively in order of appearance), and to the Htelo duplex sequence, as measured by phage ELISA. All ELISA procedures were carried out in the presence of 150 mM $K^+$, to stabilise G-quadruplexes.

The aligned sequences are shown in FIG. 3. The clones appear to have a significant degree of sequence similarity which is indicative of a successful selection process and suggests analogous functions for each clone. Control binding assays confirm that neither the phage nor the Zif268 are able to bind to Biotin-Htelo.

The sequence composition of the zinc finger helices from Zif268 is also shown for comparison in FIG. 3. The palindromic charge distributions of the selected zinc fingers are very different to that of Zif268. It is interesting to note that finger 2 (F2) of Gq1-4 have each selected negatively charged acidic sidechains (Asp or Glu) particularly in positions labelled −1 3 and 6 (FIG. 3). This pattern is unusual for DNA-binding zinc fingers as negatively charged residues are expected to repel the surface of the phosphodiester backbone. Without wishing to he bound by theory, it is possible that these acidic residues interact with guanine —NH groups which line all four grooves of an antiparallel G-quadruplex's helical core.

Zinc finger protein molecule(s) selected from this library according to the invention bind to single stranded human telomeric DNA with an affinity comparable to that of natural transcription factors.

There is strong discrimination between the double-stranded form of the same sequence and single-stranded variants.

Example 2

Molecules According to the Invention Selectively Bind G-quadruplex DNA

The nucleic acid binding properties of zinc finger molecules produced according to the invention may be analysed.

Characterisation of the binding properties of molecules Gq1-4 (see Example 1) shows that they do indeed behave very similarly. Therefore, only one phage clone (Gq1) is used to explore the binding specificity in more detail in this Example.

Phage ELISA is performed using analogues of the Biotin-Htelo oligonucleotide which contain adenine or inosine substitutions for critical guanine residues which are important for G-quadruplex formation (see Table 1). Although adenine and inosine are structurally related to guanine, both destabilise G-quadruplex formation (Williamson. J. R., Raghuraman, M. K., & Cech, T. R. (1989) Cell 59, 871–880.). The adenine substitution leads to a hydrogen bonding arrangement that is incompatible with G-quartet formation, while inosine lacks an N-2 exocyclic amino group required for fully stabilising such structures.

The phage ELISA used herein is adapted from previous assays (Choo. Y., & Klug, A. (1 994) Proc. Natl. Acad. Sci. USA. 91, 11 163–11 167.). 5'-biotinylated DNA sites are added to streptavidin-coated ELISA wells (Bochringer-Mannheim) in 50 mM potassium phosphate buffer (pH 7.5) containing 100 mM potassium chloride and 50 µM Zinc chloride (K/Zn buffer). Phage solution [overnight bacterial culture supernatant diluted 2:10 in K/Zn buffer containing 2% (w/v) fat-free dried milk (Marvel), 1% (v/v) Tween and 20 µg/ml sonicated salmon sperm DNA] was applied to each well (50 µl /well). The phage are allowed to bind for 1 hour at 20° C. Unbound phage are removed by washing 6 times with K/Zn buffer containing 1% (v/v) Tween, and then 3 times with K/Zn butler. Bound phage are detected by ELISA using horseradish peroxidase-conjugated anti-M13 IgG (Pharmacia Biotech), and the colorimetric signal was quantified using BIO KINETICS READER EL 340 (Bio-Tck Instruments).

Under the binding assay conditions used (150 mM K$^+$), Gq1 has an apparent ELISA dissociation constant ($K_d^E$) of 26 nM for Biotin-Htelo (eg. see Table 1, FIG. 4). No significant binding of Gq1 is observed for any of the guanine-substituted analogues employed, suggesting Gq1 is highly structure-specific for G-quadruplex nucleic acid.

A double stranded Htelo oligonucleotide ligand is made by DNA polymerase primer extension of the C-rich complementary sequence of Htelo. This complex is also analysed for binding of G1q by ELISA and exhibits no significant binding (Table 1). Therefore, although Gq1 is specific for the Htelo sequence, it cannot bind this sequence in the double-helical conformation.

Thus, molecules according to the invention bind G-quadruplex nucleic acid in a highly structure-specific manner.

The characteristics of this Example of a molecule according to the invention are further investigated using electromobility shift assays on G-quadruplex DNAs and DMS protection of the DNA-protein complex.

To explore the nature of the Gq1-Htelo complex in more detail, the gene encoding Gq1 is cloned and overexpressed as a glutathione-S-transferase fusion protein ('Gq1*') in E. coli (Chittenden T, Livingston D M, Kaelin W G Jr (1991) Cell Jun 14;65(6):1073–82; Smith D B, Johnson K S (1988) Gene Jul 15;67(l):31–40).

The zinc finger gene is amplified by PCR, using 1 µl overnight bacterial culture supernatant (containing phage) as template. The primers introduced BamHI sites for ligation into vector pGEX-3X (Amersham-Pharmacia). The resulting construct (Gq1*), coding for GST fused in frame with C-terminal zinc fingers, is cloned in E. Coli TG1 and verified by DNA sequencing. Fusion protein expression is then carried out in E. coli BL21 DE3. Gq1* is purified from bacterial lysates by affinity chromatography using Glutathione Sepharose 4 Fast Flow (Pharmacia Biotech).

The eluted protein appears as a single band of >95% total protein on a protein gel, and corresponds to the expected molecular weight of 37 kD.

The complex between Gq1* and oligonucleotide Htelo is studied by non-denaturing gel mobility shift analysis (Cann JR (1989) J Biol Chem Oct 15;264(29):17032–40. Garner M M, Revzin A (1981) Nucleic Acids Res Jul 10;9(13)3047–60) as follows;

Gel Mobility Shift Analysis

Binding reactions are performed in a final volume of 10 µl, using 10 fmol of labelled oligonucleotide and various amounts of purified Gq1* in binding buffer: 20 mM Tris-HCl pH 7.5, 1 mM EDTA, 1 mM DTT, 6% glycerol, 100 µg/ml BSA, 1 µg/ml calf thymus DNA, 50 µM ZnCl$_2$ and KCl to 150 mM. Binding reactions are carried out at room temperature for 1 hour. The samples are loaded on a 8% polyacrylamide (acrylamide:bisacrylamide=33:1) non-denaturing gel. The buffer in the gel and for electrophoresis is 0.5 X TB buffer (Sambrook, J., Fritsch, E. F., & Maniatis, T. (1989) in Molecular Cloning, A Laboratory Manual, Cold Spring Harbor Laboratory Press, Cold Spring Harbor.). Electrophoresis is performed at 15 V/cm, for 2 hours, at 4° C. The gels are exposed in a phosphorimager cassette and imaged (Model 425E PhosphorImager; Molecular Dynamics, Inc). The bands are quantified using Imagequant software. The fraction of DNA that is bound and free is determined after normalization by summing the total number of counts in each lane (Senear D F, Brenowitz M (1991) J Biol Chem Jul 25;266(21):13661–71). To minimise any error due to perturbation of the equilibrium under electrophoretic conditions, the fraction of free DNA is measured at various protein concentrations rather than measuring the amount of complex formed (Cann J R (1989) J Biol Chem Oct 15;264(29):17032–40; Garner M M, Revzin A (1981) Nucleic Acids Res Jul 10;9(13):3047–60). The data is plotted as Ø (1-fraction of free DNA) vs protein concentration to determine the $K_d$, which is equal to the protein concentration at which half the flee DNA is bound. Equilibrium dissociation constants ($K_d$) are extracted by non-linear regression using the program Origin 4.1 and the following equation (Gunasekera A, Ebright Y W, Ebright R H (1992) J Biol Chem Jul 25;267(21):14713–20)

$$\emptyset = [P]/\{K_d + [P]\}$$

where Ø denotes the fractional saturation of DNA (i.e. fraction of DNA complexed with the protein). [P] represents the protein concentration in the experiment. Ø and [P] were inputs to the non-linear regression; $K_d$ was an unconstrained output.

Figure 5A:
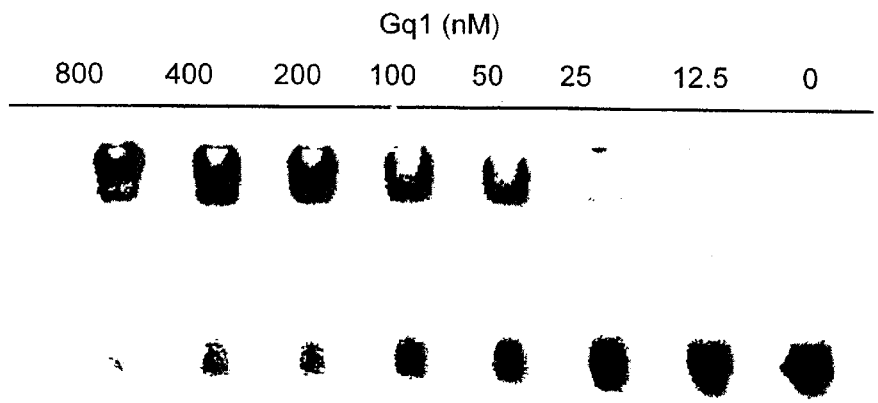
FIG. 5a shows gel mobility shift assay of Gq1* binding to Htelo. The analysis was carried out in 8% non-denaturing polyacrylamide gel at 4° C. The DNA concentration is fixed at 1 nM while the amount of protein added to the binding reaction is varied as follows: 800 nM (lane 1), 400 nM (lane 2), 200 nM (lane 3), 100 nM (lane 4), 50 nM (lane 5), 25 nM (lane 6), 12.5 nM (lane 7) and 0 nM (lane 8)

Various concentrations of Gq1* are incubated with 5' $^{32}$-labelled-Htelo, under conditions (150 mM K$^+$) that promote and stabilise the G-quadruplex conformation, and the resulting complex is run on an 8% non-denaturing polyacrylamide gel (see for example FIG. 5a). This analysis shows the transition of a low molecular weight band to a single, higher molecular weight species upon increasing Gq1* concentration.

Figure 5B:
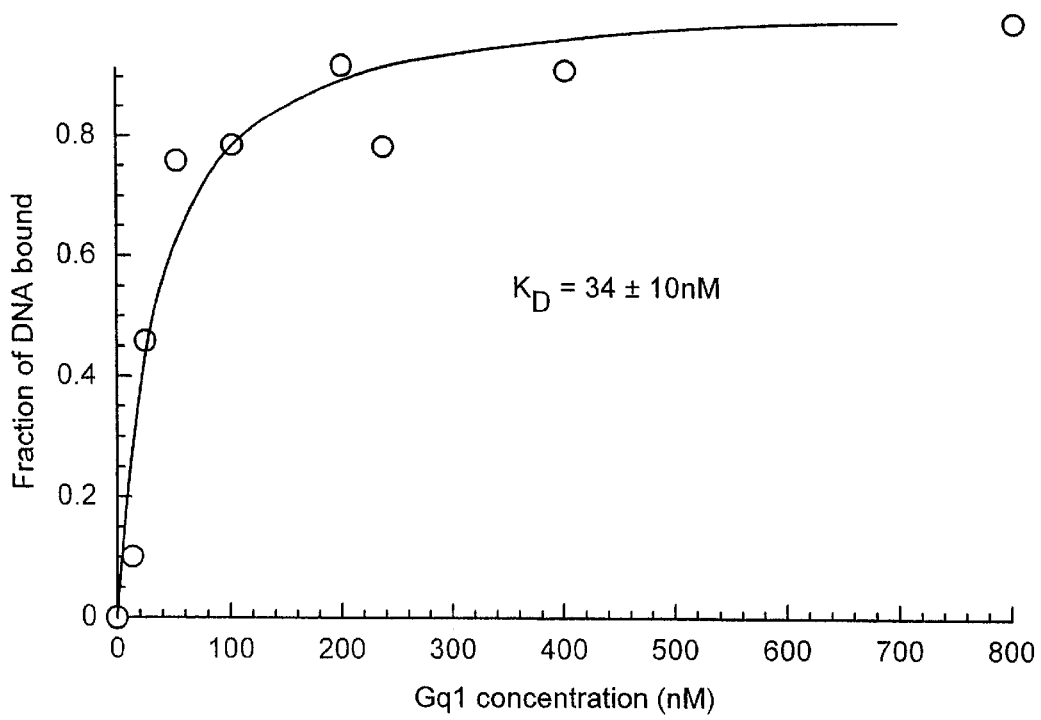
FIG. 5b shows apparent equilibrium binding curve obtained by calculating the fraction of Htelo bound at varying Gq1* concentrations (Imagequant software). The binding constant was determined by fitting to the equation $\emptyset=[P]/\{K_d+[P]\}$ as described in the Examples.

The gel mobility shift data was fitted to a quadratic (see above—Gunasekera A. Ebright Y W, Ebright R H (1992) *J Biol Chem* Jul 25;267(21):14713–20) and equilibrium dissociation constants ($K_d$) are extracted by non-linear regression, to give an observed dissociation constant ($K_d$) of 34±10 nM (FIG. 5b) which is close to the apparent EL1SA value ($K_d^E$) of 26 nM. No DNA-binding is observed for GST protein alone in the absence of Gq1.

To elucidate the conformation of the oligonucleotide in the Gq1*-Htelo complex, DMS protection experiments are carried out on the complexin the form of Dimethyl sulfate protection assay of Htelo and Htelo-Gq1zinc finger complexes.

Htelo is 5'-labelled with $^{32}$P and is denatured by heating at 95° C. for 10 minutes. Annealing/quadruplex forming reactions are carried out as described above, in 50 mM Tris-HCl buffer with or without 150 mM potassium. DMS protection is carried out as described by Maxam and Gilbert (Maxam, A. M., & Gilbert, W. (1980) *Methods Enzymol*. 65, 499–560.). 1 µl of dimethylsulfate (DMS) is added to 20 pmol of annealed Htelo, at 4° C., in 200 µl of appropriate buffer. The mixture is incubated at 20° C. for 5 minutes. Reactions are stopped by adding ¼ volume of stop buffer containing 1M β-mercaptocthanol and 1.5 M sodium acetate, pH 7.0. The reaction products are ethanol precipitated twice and treated with 100 µl of 1M piperidine at 90° C. for 30 min. The cleaved products are resolved on a 20% denaturing urea-polyacrylamide gel.

For DMS footprinting of the Htelo-Gq1 zinc finger complex, the procedure described above was adapted: 2 µl of DMS are added to 0.2 pmol of annealed litelo, in the absence or presence of 500 nM purified Gq1* (see below), in 200 µl of the appropriate buffer, containing 1 µg/ml calf thymus DNA. Reactions are carried out for 10 minutes at 20° C., after which the procedure continues as described above.

Using 5' $^{32}$-labelled-Htelo and buffer containing 100 mM K⁺, the concentration of Gq1* was set at 200 nM which is ~6-fold higher than the $K_d$. These conditions correspond to a near total bandshift (FIG. 5a), representing complete complexation of the DNA.

Figure 6:
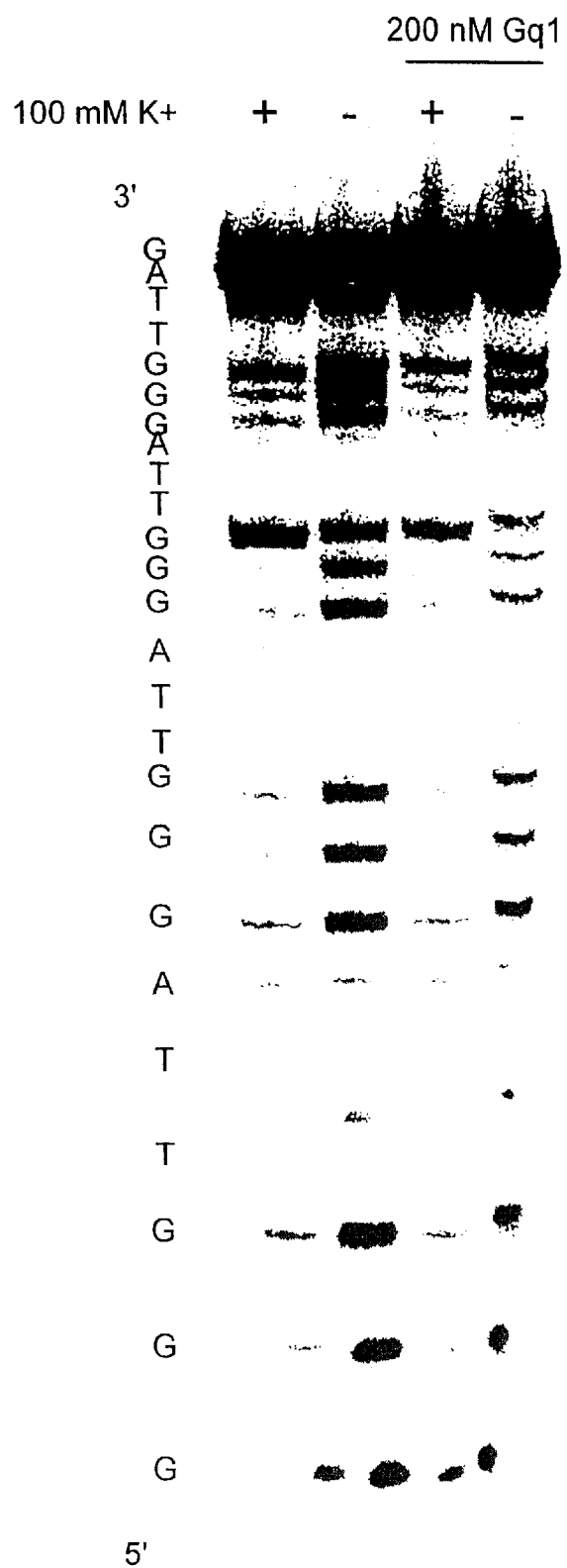
FIG. 6 shows DMA methylation protection analysis of Htelo in the presence of Gq1* protein. Htelo (SEQ ID NO: 5) was annealed in 100 mM $K^+$ or 50 mM Tris-HCl, and methylation protection patterns were obtained in the presence or absence of 200 nM Gq1* (ie. 200 nM Gq1*—a concentration giving approximately full shift). DNA concentration is 1 nM. Each sample was incubated with DMS for 5 min. Fragments formed by piperidine cleavage of methylated guanines, were resolved on a 20% polyacrylamide gel. Lane 1: methylation pattern of Htelo in the presence of 100 mM $K^+$; Lane 2: reference methylation pattern of Htelo in the absence of $K^+$; Lane 3: methylation pattern of Htelo in the presence of 100 mM $K^+$ and incubation with 200 nM Gq1*; Lane 4: methylation pattern in the absence of $K^+$, incubated with 200 nM Gq1*.

In the absence of Gq1*, a cleavage protection pattern is generated that is both characteristic of G-quadruplex structure, and that is dependent on the presence of 100 mM K⁺ (FIG. 6; lanes 1 and 2). However, in the presence of Gq1* and 100 mM K⁺, there is still significant protection of the critical guanines (FIG. 6; lane 3) indicative of G-quadruplex structure. Furthermore, in the absence of potassium, the protein does not alter the unfolded state of Htelo (FIG. 6; lane 4).

Thus it is demonstrated that Gq1 binds Htelo in the G-quadruplex conformation, and that this protein molecule according to the invention recognises the structure of folded G-quadruplex.

Example 3

Use of Molecules According to the Invention in a Telomerase Assay

Telomerase activity may be assayed according to the invention using the following method.

Telomerase template primers are bound to ELISA wells by biotin-streptavidin linkage as described in Example 2. These primers are non-G-rich and are not bound by Gq1*.

Test extracts are added to wells in telomerase extension buffer.

The test extracts may contain telomerase activity. Such activity would cause primer extension through the addition of repeats of the sequence [(GGGTTA)n].

A telomerase extension reaction is carried out in telomerase extension conditions.

Telomerase products [(GGGTTA)n] are detected by ELISA as described in Example 2.

This method provides a convenient and rapid technique for the assay of telomerase activity, and/or the detection of candidate telomerase activities.

Sequence Listing

SEQ. ID. No. 1 GGTTAG GGTTAG GGTTAG GGTTAG GGTTAG

SEQ. ID. No. 2 TATANNNNNNNGGCGTGTCACAGT-CAGCTTCAACGTC

SEQ. ID. No.3 TATGTGCGGNNNNNNNTCACAGT-CAGTCCACACGTC

SEQ. ID. No.4 TATANNNNNNNNNNNNNTCACAGT-CAGTCCACACGTC

---

What is claimed is:

1. An isolated Cys2 His2 zinc finger polypeptide that binds to a molecule selected from the group consisting of telomeric nucleic acid, G-quadruplex nucleic acid and G-quartet nucleic acid.

2. A zinc finger polypeptide according to claim 1 wherein said nucleic acid is not in a double-helical conformation.

3. A zinc finger polypeptide according to claim 1 wherein said nucleic acid comprises single-stranded DNA.

4. A zinc finger polypeptide according to claim 1 wherein said nucleic acid is contained in a chromosome end.

5. A zinc finger polypeptide according to claim 1 wherein said nucleic acid is in a non-Watson-Crick base paired conformation.

6. A zinc finger polypeptide according to claim 1 wherein said nucleic acid comprises Hoogsteen base pairing.

7. A zinc finger polypeptide according to claim 1 wherein said zinc finger polypeptide comprises at least one zinc finger motif.

8. A zinc finger polypeptide according to claim 1 wherein said polypeptide has an affinity for G-quadruplex nucleic acid which is different from its affinity for duplex nucleic acid.

9. A method for assaying telomerase activity, said method comprising
   (i) providing a sample of nucleic acid substrate for telomerase;
   (ii) contacting said nucleic acid sample with a telomerase;
   (iii) contacting said nucleic acid sample with a zinc finger polypeptide according to claim 1; and
   (iv) monitoring the binding of said zinc finger polypeptide to said telomerase treated nucleic acid sample.

10. A method according to claim 9 wherein said assay method comprises an ELISA assay.

11. A method according to claim 10 wherein said assay method is in micro-well format.

12. A method for estimating the length of telomere(s), said method comprising
   (i) contacting said telomere(s) with a zinc finger polypeptide according to claim 1;
   (ii) monitoring the binding of said zinc finger polypeptide to said telomere; and
   (iii) estimating the length of said telomeres from the strength of said binding.

13. A method according to claim 12 wherein said method comprises an ELISA assay.

14. A method according to claim 12 wherein said method is in micro-well format.

15. A method for discriminating between duplex and quadruplex nucleic acid comprising contacting a sample of nucleic acid with a zinc finger polypeptide according to claim 8 and monitoring the binding of said zinc finger polypeptide to said nucleic acid.

16. A method according to claim 15 wherein said method comprises an ELISA assay.

17. A method according to claim 15 wherein said method is in micro-well format.

18. A zinc finger polypeptide according to claim 1 which is labelled.

19. A method for detecting telomeres in vivo comprising
   (i) contacting a labelled zinc finger polypeptide according to claim 18 with nucleic acid in vivo wherein said labelled zinc finger polypeptide has an affinity for G-quadruplex nucleic acid which is different from its affinity for duplex nucleic acid; and
   (ii) monitoring binding of said labelled zinc finger polypeptide to said nucleic acid.

20. A method according to claim 19 wherein said method comprises an ELISA assay.

21. A method according to claim 19 wherein said method is in micro-well format.

22. A method for manipulating telomeres in vivo comprising contacting a labelled zinc finger polypeptide according to claim 18 with a telomere, wherein said zinc finger polypeptide further comprises an effector domain.

* * * * *

SEQUENCE LISTING

<160> NUMBER OF SEQ ID NOS: 24

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ggttagggtt agggttaggg ttagggttag                          30

<210> SEQ ID NO 2

```
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (5)..(11)
<223> OTHER INFORMATION: a, t, c, or g

<400> SEQUENCE: 2
tatannnnnn nggcgtgtca cagtcagctt caacgtc                              37

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (10)..(16)
<223> OTHER INFORMATION: a, t, c, or g

<400> SEQUENCE: 3
tatgtgcggn nnnnnntcac agtcagtcca cacgtc                               36

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (5)..(17)
<223> OTHER INFORMATION: a, t, c, or g

<400> SEQUENCE: 4
tatannnnnn nnnnnnntca cagtcagtcc acacgtc                              37

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gggttagggt tagggttagg gttag                                           25

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ser Ala His Leu Thr Arg
  1               5

<210> SEQ ID NO 7
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Asp Arg Ser Asp Leu Ser Glu
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp His Arg Ile Glu
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp His Leu Ile Asn
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Arg Ala Asp Leu Ser Glu
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Ser His Arg Thr Asn
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ser Ala His Leu Thr Arg
  1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Asp His Leu Ser Glu
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Ser His Arg Thr Asn
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser His His Leu Ile Gln
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Ala Asp Leu Ser Glu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Gln His Tyr Arg Thr Asn
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

Arg Ser Asp Glu Leu Thr Arg
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp His Leu Thr Thr
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Asp Glu Arg Lys Arg
 1               5

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggttaaggtt aaggttaagg ttaaggttaa                                    30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agttagagtt agagttagag ttagagttag                                    30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (1)
<223> OTHER INFORMATION: inosine
<221> NAME/KEY: modified_base
<222> LOCATION: (7)
<223> OTHER INFORMATION: inosine
<221> NAME/KEY: modified_base
<222> LOCATION: (13)
<223> OTHER INFORMATION: inosine
<221> NAME/KEY: modified_base
<222> LOCATION: (19)
<223> OTHER INFORMATION: inosine
<221> NAME/KEY: modified_base

```
<222> LOCATION: (24)
<223> OTHER INFORMATION: inosine

<400> SEQUENCE: 23
ngttagngtt agngttagng ttagngttag                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Telomeric
      oligonucleotide

<400> SEQUENCE: 24
gttagggtta gggttagggt tagggttagg                                          30
```